United States Patent [19]

Auman

[11] Patent Number: 5,196,549
[45] Date of Patent: Mar. 23, 1993

[54] POLYETHERS BASED ON 9,9-BIS-PERFLUOROALKYL-3,6-DIHYDROXY-XANTHENE OR 9-ARYL-9-PERFLUOROALKYL-3,6-DIHYDROXY-XANTHANE

[75] Inventor: Brian C. Auman, Newark, Del.

[73] Assignee: E. I. Du Pont de Nemours and Company, Wilmington, Del.

[21] Appl. No.: 714,222

[22] Filed: Jun. 11, 1991

[51] Int. Cl.$^5$ ................... C07D 209/48; C07D 311/82
[52] U.S. Cl. ...................................... 548/462; 549/388
[58] Field of Search ........................... 549/388; 548/462

[56] References Cited

U.S. PATENT DOCUMENTS

| | | | |
|---|---|---|---|
| 3,968,083 | 7/1976 | Quinn | 260/47 CP |
| 4,433,104 | 2/1984 | Giles, Jr. | 525/180 |
| 4,546,141 | 10/1985 | Gebauer | 524/401 |
| 4,578,427 | 3/1986 | Saito et al. | 525/150 |
| 4,612,361 | 9/1986 | Peters | 528/185 |
| 4,912,166 | 3/1990 | Stewart | 525/151 |
| 4,942,216 | 7/1990 | Heintz et al. | 528/125 |

OTHER PUBLICATIONS

CA105:24822g Aromatic copolyesters. Yatsu et al. p. 14, 1986.

Primary Examiner—Mary C. Lee
Assistant Examiner—Joseph K. McKane

[57] ABSTRACT

Polyethers based on 9,9-bis-perfluoroalkyl-3,6-dihydroxy-xanthene or 9-aryl-9-perfluoroalkyl-3,6-dihydroxy-xanthene and another constituent selected from aryl, sulfone, aryl ketone, benzonitrile, and imide. These polyethers are useful as dielectric films in electronic devices.

5 Claims, No Drawings

POLYETHERS BASED ON 9,9-BIS-PERFLUOROALKYL-3,6-DIHYDROXY-XANTHENE OR 9-ARYL-9-PERFLUOROALKYL-3,6-DIHYDROXY-XANTHANE

FIELD OF THE INVENTION

This invention relates to polyethers and electronic devices using polyethers based on 9,9-bis-perfluoroalkyl-3,6-dihydroxy-xanthene or 9-aryl-9-perfluoroalkyl-3,6-dihydroxy-xanthene and another constituent selected from the group consisting of aryl sulfone, aryl ketone, benzonitrile, imide, and mixtures thereof.

BACKGROUND OF THE INVENTION

Polymers being characterized by high thermal stability, inert character, low coefficient of thermal expansion, low water absorption, low dielectric constant, and various degrees of Tg, among other properties, are very desirable.

These polymers may find applications requiring specific groups of the aforementioned characteristics. Recently, this need has started increasing dramatically in electronic devices. With continuously escalating sophistication in such devices, the demands on the properties and the property control are becoming rather vexatious. Especially for the electronics industry, improvements of polymers are needed in forming tough, inert, thermally stable, pin-hole free coatings, having low dielectric constant, low coefficient of thermal expansion, low moisture absorption, and high Tg, among others. Although it is not usually possible to maximize all properties, since many of them may be antagonistic, optimization as a total is highly desirable and it may be achieved if adequate control on the properties becomes available through molecular architecture or other means.

It has now been found that polyethers based on 9,9-bis-perfluoroalkyl-3,6-dihydroxy-xanthene or 9-aryl-9-perfluoroalkyl-3,6-dihydroxy-xanthene and another constituent selected from the group consisting of aryl sulfone, aryl ketone, benzonitrile, imide, and mixtures thereof, represent a class of valuable polymers promoting such properties, which are very desirable in the electronics industry.

The following references, among others, disclose polyether sulfones, polyether ketones, polyetherimides, and the like, but they do not mention, suggest, or imply the critical combinations utilized according to the present invention.

U.S. Pat. No. 4,546,141 (Gebauer) discloses a primer coating composition which is claimed to be particularly suitable for topcoating with fluorocarbon polymers. This primer composition contains (a) 100 parts by weight of a copolymer of tetrafluoroethylene, perfluoro(alkylvinyl) ethers and if appropriate hexafluoropropylene or vinylidene fluoride, (b) 10 to 250 parts by weight of a mixture of lithium hydroxide and finely divided silicon dioxide produced by thermal treatment, (c) 10 to 1000 parts by weight of at least one thermoplastic resin from the group comprising the polyarylene sulfide resins, the aromatic polyether-sulfone resins and the aromatic polyether-ketone resins and (d) water as a liquid carrier.

U.S. Pat. No. 4,578,427 (Saito et al.) discloses a coating resin composition comprising from 50 to 99% by weight of a thermoplastic aromatic polyether ketone resin and from 50 to 1% by weight of a perfluoroalkoxy resin or a tetrafluoroethylene/ hexafluoropropylene copolymer resin having hexafluoropropylene content of from 18 to 25% by weight. The composition, when applied to a steel plate, for example, produces a coating film which is claimed to be greatly improved in water repellency, while retaining the desirable properties of the polyether ketone, such as high heat resistance, good mechanical and electrical properties, and high chemical resistance.

U.S. Pat. No. 4,912,166 (Stewart) discloses a blend of tetrafluoroethylene and a poly(oxy-p-phenyleneisophthaloyl-phenylene/oxy-p-phenyleneterephthaloyl-p-phenylene) (PEKK), which is claimed to result in improved processing of the fluoroelastomer at temperatures below the melting temperature of the PEKK and improved physical properties of cured fluoroelastomer.

U.S. Pat. No. 4,942,216 (Heinz et al.) discloses polyaryl ether ketones claimed to have improved processibility.

U.S. Pat. No. 3,968,083 (Quinn) discloses polyetherimides derived from the reaction of an organic diamine and a class of dianhydrides selected from the class consisting of a bisphenol fluorenone dianhydride and a phenolphthalein dianhydride.

U.S. Pat. No. 4,433,104 (Giles, Jr.) discloses blends of (a) a polyetherimide and (b) a thermoplastic fluorinated polyolefin, or copolymer thereof.

These blends are claimed to have good flexural strength and flexural modulus, and to have higher impact strength than those associated with the polyetherimide components of the blends.

U.S. Pat. No. 4,612,361 (Peters) discloses fluoro-containing polyetherimides prepared from bis etherdianhydrides, fluoro-containing dianhydrides, and organic diamines. The copolymers are claimed to exhibit both increased Tg and increased solubility in halogenated solvents, which enhances their value in a wide variety of uses including films, molding compounds, and coatings.

SUMMARY OF THE INVENTION

The instant invention is directed to compositions comprising a polyether of the structure:

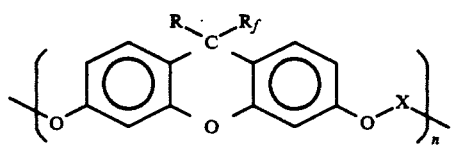

wherein $R_f$-perfluoroalkyl of 1–16 carbon atoms,

R is selected from the group consisting of aryl, substituted aryl, and perfluoroalkyl of 1–16 carbon atoms, n is an integer, n is an integer, and —X— is a bivalent radical selected from the group consisting of aryl sulfone radical, aryl ketone radical, imide radical and mixtures thereof.

Preferably, the aryl sulfone radical has the structure:

the aryl ketone radical has the structure:

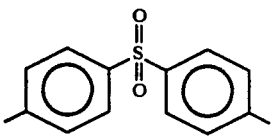

and the imide radical has the structure:

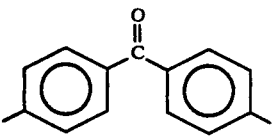

wherein Z is a bivalent aromatic radical.

The present invention also pertains to electronic devices containing a conductor or semiconductor comprising:

(a) a substrate which comprises a conductor, semiconductor or insulator; and (b) a dielectric film in contact with at least a portion of the substrate, the dielectric film comprising a polyether of the structure:

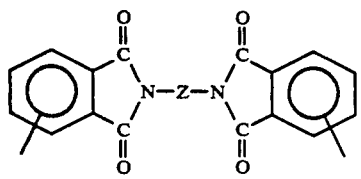

wherein $R_f$ is perfluoroalkyl of 1–16 carbon atoms,

R is selected from the group consisting of aryl, substituted aryl, and perfluoroalkyl of 1–16 carbon atoms, and —X— is a bivalent radical selected from the group consisting of aryl sulfone radical, aryl ketone radical, benzonitrile radical, imide radical and mixtures thereof.

Preferred definitions for the aryl sulfone radical, the aryl ketone radial and the imide radical are as set forth previously. In addition a preferred definition for the benzonitrile radical is

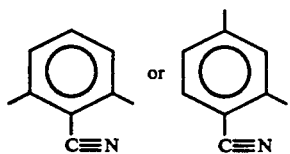

DETAILED DESCRIPTION OF THE INVENTION

The instant invention is directed to polyethers based on 9,9-bis-perfluoroalkyl-3,6-dihydroxy-xanthene or 9-aryl-9-perfluoroalkyl-3,6-dihydroxy-xanthene and another constituent selected from the group consisting of aryl sulfone, aryl ketone, benzonitrile, imide, and mixtures thereof. It is also directed to electronic devices utilizing these polyethers.

In general, the polyethers of the instant invention may be prepared by reacting 9,9-bis-perfluoroalkyl-3,6-dihydroxy-xanthene or 9-aryl-9-perfluoroalkyl-3,6-dihydroxy-xanthene with another constituent selected from the aforementioned group, which constituent comprises two —F, —Cl, or —NO$_2$ groups in para- or orthoposition with respect to an electron withdrawing group, such as =SO$_2$ in the case of sulfone, =CO in the case of ketone, —C≡N in the case of benzonitrile, and =CO in the case of the imide.

Other electron withdrawing groups, which may be used to activate the —F, —Cl, or —NO$_2$ groups in similar reactions as discussed above, are perfluorinated groups, and

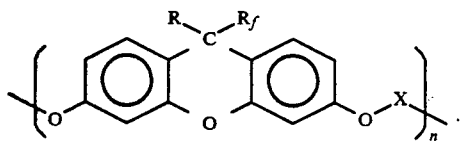

Since the reactivity of the —F groups is typically higher than that of the —Cl or —NO$_2$ groups, it is preferable to use the fluorocompounds for this reaction. However, by proper selection of solvent and temperature conditions, the chloro- and nitrocompounds may be also used. The preference may lean toward the latter compounds if cost is an issue in the selection process, since the chloro- and nitrocompounds are usually less expensive than the respective fluorocompounds.

Sometimes end-capping may be desired for improved stability. This may be achieved by addition a small amount of a monofunctional constituent (similar to the bifunctional constituent described above) during or preferably at the end of the reaction, in order to remove the remaining reactive end-groups.

Thus, as shown in Example 1, polyethers of the present invention containing aryl sulfone units may be prepared by reacting preferably equimolar amounts of 9,9-bis-perfluoroalkyl-3,6-dihydroxy-xanthene or 9-aryl-9-perfluoroalkyl-3,6-dihydroxy-xanthene, such as for example 9,9-bis(perfluoromethyl)-3,6-dihydroxy-xanthene (BXDO) and a difluoroarylsulfone, such as for example 4,4'-difluorodiphenylsulfone (DFDPS). The monomers may be dissolved in an appropriate solvent, such as dimethylacetamide (DMAC), for example. Preferably, base, such as for example anhydrous potassium carbonate is also added to form the reactive phenolate of the dihydroxy compound. A solvent capable of forming azeotropic mixtures with water, such as for example toluene, xylene, and the like may be used for removal of any water present. This solvent is preferably removed after it fulfills its purpose of removing the water, and the mixture is heated until the reaction is complete.

The polyether may then be isolated, for example by precipitation in water, dissolution in a suitable solvent, such as N-methyl-2-pyrrolidone for example, filtration to remove insoluble matter, reprecipitation in a suitable nonsolvent, such as water and/or methanol for example, filtration, and drying.

Example 2 demonstrates the lower reactivity of the chloro-derivative as compared to the respective fluoroderivative of a sulfone constituent.

Among other publications, the following deal with synthetic methods regarding polyethersulfones.

Johnson et al., Poly(aryl Ethers) by Nucleophylic Aromatic Substitution. I. Synthesis and Properties, *Journal of Polymer Science*, Vol. 5, 2375-2398 (1967).

Jennings et al., Poly(Arylene Sulfones) and Poly(Arylene Ketones) by Reactions Involving Substitution at Aromatic Nuclei, *Journal of Polymer Science: Part C*, No. 16, pp. 715-724 (1967).

In a similar manner to that given in Example 1, a polyetherketone may be prepared by the reaction of 9,9-bis-perfluoroalkyl-3,6-dihydroxy-xanthene or 9-aryl-9-perfluoroalkyl-3,6-dihydroxy-xanthene with a respective ketone containing bisubstituted constituent. Depending on the ketone containing constituent, the solubility and tendency of the resulting polyetherketone to crystallize may vary, and a different solvent and/or higher temperatures may be required to obtain high molecular weight polymer. Solvents such as NMP, dimethylsulfoxide (DMSO), sulfolane, dimethylsulfone, diphenylsulfone or other polar aprotic solvents are good choices for this purpose. Use of chlorine in place of fluorine, as for example in 4,4'-dichlorobenzophenone, due to lower reactivity necessitates higher reaction temperatures for obtaining high molecular weight polyethers. If higher temperatures are necessary, another solvent besides toluene which facilitates water removal from the system should be used. Solvents like xylenes, chlorobenzene and other aromatic hydrocarbons are useful for this purpose.

Examples of preferred ketone containing difunctional constituents are:
4,4'-difluorobenzophenone (DFBP);
1,3-bis(4-fluorobenzoyl)benzene;
1,4-bis(4-fluorobenzoyl)benzene;
4,4'-bis(4-fluorobenzoyl)benzophenone;
4,4'-bis(4-fluorobenzoyl)phenyl phosphine oxide;
2,6-bis(4-fluorobenzoyl)naphthalene;
1,3-bis(4-fluorophenoxy-4'-benzoyl)benzene;
1,4-bis(4-fluorophenoxy-4'-benzoyl)benzene;
4,4'-bis(4-fluorophenoxy-4'-benzoyl)benzophenone;
4,4'-bis(4-fluorophenoxy-4'-benzoyl)diphenylether;
2,6-bis(4-fluorophenoxy-4'-benzoyl)naphthalene;
and mixtures thereof.

Among other publications, the following give synthetic methods and monomers regarding polyether ketones.

Mullins et al., "The Synthesis and Properties of Poly(Aromatic Ketones)", *JMS-Rev. Macromol. Chem. Phys.*, C27(2), 313-341 (1987);

Atwood et al., "Synthesis and Properties of Polyaryletherketones", *Polym. Prepar.*, 20, 191-194 (1979); and Atwood et al., "Synthesis and Properties of Polyaryletherketones", *Polymer*, Vol. 22, 1096-1103 (1981).

A polyether containing a benzonitrile constituent may be similarly prepared by reaction of 9,9-bis-perfluoroalkyl-3,6-dihydroxy-xanthene or 9-aryl-9-perfluoroalkyl-3,6-dihydroxy-xanthene, such as for example BXDO with a respective difluoroderivative, such as for example 2,6-difluorobenzonitrile, in a similar manner to that shown in Example 1. As aforementioned, a different solvent and/or higher temperature may be necessary to optimize molecular weight, depending on the particular derivative used. Examples of other similar monomers, with activated groups, are 2,6-dichlorobenzonitrile or 2,6-dinitrobenzonitrile, as well as 2,4-dichlorobenzonitrile or 2,4-dinitrobenzonitrile. However, the relative reactivity of these monomers is typically lower, and therefore more severe conditions may be needed to obtain high molecular weight polyethers as already described.

A polyetherimide may be directly prepared by the reaction of 9,9-bis-perfluoroalkyl-3,6-dihydroxyxanthene or 9-aryl-9-perfluoroalkyl-3,6-dihydroxyxanthene, such as for example BXDO with a respective dinitro diimide constituent such as for example bis(4-nitrophthalic)-4,4'-diaminodiphenylether diimide, in a similar manner to that given in Example 1. Again, depending on the particular derivative of the constituent which is used, a different solvent and/or higher temperature may be necessary to optimize molecular weight.

Since many times side-reactions may occur due to the by-product nitrite salts that are formed during the reaction, which by-products may be difficult to remove from the polyether, an alternative procedure in preparing the polyether may be used.

According to this alternative process, BXDO, for example, is reacted with 4-nitrophthalimide, e,g., 4-nitro-N-methylphthalimide) or 4-phthalonitrile, for example, followed by hydrolysis of the imide or nitrile groups and subsequent cyclodehydration to form a dianhydride. This dianhydride after purification is then reacted with a diamine, like for example a diamine selected from the preferred list below, in a solvent like N-methyl-2-pyrrolidone (NMP) or dimethylacetamide (DMAC) to give a polyetheramic acid which can be thermally or chemically imidized to the polyetherimide, as known in the art. Alternatively, the anhydride is heated with the diamine in a solvent like m-cresol or NMP at 150°-200° C. to give the polyimide in one step often with the aid of a co-solvent like N-cyclohexyl-2-pyrrolidone (CHP), toluene or xylene to facilitate water removal.

Examples of preferred diamines in the formation of the imide part of the polyether of the present invention are 4,4'-diaminodiphenylether, 3,3'-dimethyl-4,4'-diaminobiphenyl, 3,3'-dimethoxy-4,4'-diaminobiphenyl, 4,4'-diaminoparaterphenyl, 4,4'-bis(4-aminophenoxy)-biphenyl, 4,4'-diaminodiphenylsulfone, 3,3'-diaminodiphenylsulfone, bis[4-(4-aminophenoxy) phenyl]sulfone, bis[4-(3 aminophenoxy)phenyl] sulfone, bis[2-aminophenoxy)phenyl]sulfone, 1,4-bis(4-aminophenoxy)benzene, 2,2'-dichloro-4,4'-diamino-5,5'-dimethoxy biphenyl, 2,2'-5,5'-tetrachloro benzidine, 9,10-bis(4-aminophenyl) anthracene, o-tolidine sulfone, 1,3-bis(4-aminophenoxy)benzene, 1,3-bis(3-aminophenoxy)-benzene, 1,4-bis(4-aminophenyl)benzene, bis[4-(aminophenoxy)phenyl]ether, 4,4'-diaminodiphenylmethane, bis(3-ethyl-4-aminophenyl)methane, bis(3-methyl-4-aminophenyl)methane, bis(3-chloro-4-aminophenyl)methane, 2,2'5,5'-tetrachloro-4,4'-diaminobiphenyl, 4,4'-diaminodiphenylsulfide, 3,3'-diaminodiphenyl ether, 3,4'-diaminodiphenyl ether, 4,4'-diaminodiphenylmethane, 4,4'-diaminooctafluorobiphenyl, metaphenylenediamine, 2,2-bis[4-aminophenoxy)phenyl]propane, 2,2-bis[4-(4-aminophenoxy)phenyl]hexafluoropropane, 2,2-bis(4-aminophenyl)propane, 2,2-bis(4-aminophenyl) hexafluoropropane, 2,2-bis(3-hydroxy-4-aminophenyl)-propane, 2,2-bis(3-hydroxy-4-aminophenyl)hexafluoropropane, 9,9-bis(4-aminophenyl)-10-hydroanthracene, orthotolydinesulfone, 3,3',4,4'-biphenyltetramine, 3,3',4,4'-tetraminodiphenyl ether, diaminoanthraquinone, 1,5-diaminoanthraquinone, bis[4-(4-aminophenoxy)phenyl]sulfone, bis[4-(3-aminophenoxy)phenyl]sulfone, bis[4-(2-aminophenoxy)phenyl]sulfone, 3,3'-dichloro-4,4'-diaminobiphenyl, 3,3'-dihydroxy- 4,4'diamino biphenyl, 4,4'-diaminobiphenyl, 9,9-Bis(4-aminophenyl)fluorene, 4,4'-dimethyl-3,3'diaminodiphenyl sulfone, 3,4'-Bisaniline-A, Bisaniline M, Bisaniline P, methylene-bis-2,6-xylidine, 4-diamino cumene, 2,5-dichloro p-phenylene diamine, 2,6-dichloro p-phenylene diamine, 2,5-dimethyl p-phenylene diamine, 2-chloro p-phenylene diamine, 4-chloro m-phenylene diamine, 5-chloro-2-methyl-p-phenylene diamine, Acetoguanamine, 2,3,5,6-tetramethyl-p-phenylene diamine, 2,4,6-trimethyl-m-phenylene diamine, bis-3-aminopropyl-tetramethyldisiloxane, 2,7-diaminofluorene, 2,5-diaminopyridine, p-phenylenediamine, 1,2-bis-(anilino)ethane, diaminobenzanilide, diaminobenzoate, 1,5-diaminonaphthalene, diaminotoluene, tetradine, iaminobenzotrifluoride, diaminoanthraquinone, 1,3-bis-(anilino)hexafluoropropane, 1,4-bis(anilino)octafluorobutane, 1,5-bis(anilino)decafluoropentane, 1,7-bis-(anilino)tetradecafluoroheptane, 2,2-bis[4-(3-aminophenoxy)phenyl]hexafluoropropane, 2,2-bis[4-(2-aminophenoxy)phenyl]hexafluoropropane, 2,2-bis[4-(4-aminophenoxy)-3,5-dimethylphenyl]hexafluoropropane, 2,2-bis[4-(4-aminophenoxy)-3,5-ditrifluoromethylphenyl]hexafluoropropane, p-bis(4-amino-2-trifluoromethylphenoxy)benzene, 4,4'-bis(4-amino-2-trifluoromethylphenoxy)biphenyl, 4,4'-bis(4-amino-3-trifluoromethylphenoxy)biphenyl, 4,4'-bis(4-amino-2-trifluoromethylphenoxy)diphenyl sulfone, 4,4'-bis(3-amino-5-trifluoromethylphenoxy)diphenyl sulfone, 2,2-bis[4-(4-amino-3-trifluoromethylphenoxy)phenyl]hexafluoropropane, 3,3',5,5'-tetramethylbenzidine, 3,3'-dimethoxybenzidine, 2,2'-bis(trifluoromethyl)benzidine, 2,2'-dimethylbenzidine, o-tolidine, m-tolidine, 2,2',5,5',6,6'-hexafluorotolidine, and 4,4'''-diaminoquaterphenyl, and 5-t-butyl-metaphenylenediamine, 4,4'-diaminotetramethylbyphenyl, and mixtures thereof.

Among other publications, the following deal with Synthetic methods regarding polyetherimides.

Takekoshi et al., "Polymer Synthesis via Aromatic Nitro Displacement Reaction", *Journal of Polymer Science, Polymer Chemistry Edition*, Vol.18, 3069-3080 (1980);

Hergenrother et al., "Polyimides Containing Carbonyl and Ether Connecting Groups", *Journal of Polymer Science: Part A: Polymer Chemistry*, Vol. 25, 1093-1103 (1987); and Hergenrother et al., "Polyimides Containing Carbonyl and Ether Connecting Groups. II", *Journal of Polymer Science: Part A: Polymer Chemistry*, Vol. 27, 1161-1174 (1989).

Examples of preferred solvents for the formation of the imide part of the present invention are polar organic solvents, such as sulfoxide type solvents including dimethylsulfoxide, diethylsulfoxide, and the like, formamide type solvents including N,N-dimethylformamide, N,N-diethylformamide, and the like, acetamide type solvents including N,N-dimethylacetamide, N,N-diethylacetamide, and the like, pyrrolidone type solvents including N-methyl-2-pyrrolidone, N-cyclohexyl, 2-pyrrolidone, 1,3-dimethyl-2-imidozolidione, N-vinyl-2pyrrolidone, and the like, phenolic solvents including phenol, o-, m-, p-cresol, xylenol, halogenated phenol, catechol, and the like, hexamethylphosphoramide, and a number of lactones including γ-butyrolactones. These solvents may be used alone or as a mixture. Partial use of aromatic hydrocarbons such as xylene, toluene, and the like, is also possible, and sometimes desirable, when for example removal of water as an azeotrope is needed.

As illustrated in Example 3, electronic devices, such as for example silicon wafers which may contain electronic components, such as conductors, semiconductors, insulators, and combinations thereof, may be coated with the compositions of the present invention. Other examples include printed circuits, hybrid circuits, and the like. The compositions of the present invention are not only characterized by improved electrical properties, but they also provide higher Tg, which is very desirable, especially under conditions involving high temperatures, such as for example soldering of components, and the like.

The polyethers of the present invention are also be useful in shaped articles, fibers, films, and the like in other application areas. Nevertheless, their utility as dielectric films in electronic devices is highly preferred.

The dielectric film of the present invention may serve a number of different functions, including but not limited to insulator, protective coating, stress buffer, and the like.

GLOSSARY

BXDO: 9,9-bis(perfluoromethyl)-3,6-dihydroxy-xanthene

PXDO: 9-phenyl-9-perfluoromethyl-3,6-dihydroxy-xanthene

CHP: N-cyclohexyl-2-pyrrolidone

CTE: Coefficient of Thermal Expansion

DCDPS: 4,4'-dichlorodiphenylsulfone

DFDPS: 4,4'-difluorodiphenylsulfone

DMAC: Dimethylacetamide

DMSO: Dimethylsulfoxide

DSC: Differential Scanning Calorimetry

GPC: Gel Permeation Chromatography

GPa: GigaPascal mmole: Millimole

MPa: Megapascal

NMP: N-methyl-2-pyrrolidone ppm: Parts per million

Tg: Glass transition temperature

Tm: Melting temperature

All parts and percentages are given by weight unless otherwise stated.

EXAMPLE 1

Into a reaction flask equipped with a nitrogen inlet and outlet, a mechanical stirrer, thermometer, and a Dean-Stark trap with condenser were charged 20 g (57 mmoles) of BXDO and 14.5 g (57 mmoles) of DFDPS. The monomers were then dissolved in 100 ml DMAC followed by the addition of 17.4 g (0.13 moles) anhydrous potassium carbonate and 50 ml of toluene. The reaction mixture was heated to ~135° C. and a small amount of water was removed by azeotropic distillation with the toluene. After the water removal appeared complete (1 to 2 hours) the reaction was heated to 160°-165° C., the toluene was removed via the Dean-Stark trap, and the reaction was allowed to proceed for about 4 hours. A very thick solution resulted which was diluted with 70 ml of DMAC after cooling to ~100° C. The solution was then precipitated into demineralized water, the polymer was collected by suction filtration, and then the polymer was slurried overnight in fresh demineralized water. Subsequently, the polymer was again filtered, washed with methanol, and dried. Afterwards, the polymer was dissolved in about 600 ml of NMP (low solubility noted in chloroform, methylene chloride, and tetrahydrofuran). The NMP solution was then pressure filtered to give a clear amber solution. This solution was precipitated into slightly acidified (HCl) methanol, and the solid was filtered off and dried to give a white, very fibrous polymer in 27.2 g yield (some material lost during work-up). GPC analysis of the polymer in DMAC (with 1 g toluene sulfonic acid per 4 liters of DMAC) at 135° C. gave an Mn=62500 and Mw=282000 based on polystyrene. The Mw/Mn was 4.51 due to the presence of a small low molecular weight tail. DSC analysis at 10° C./min revealed a Tg of 240° C. H-NMR analysis (DMSO-$d_0$ AT 50° C.) was consistent with the expected polymer structure with peaks at 7.3 ppm (doublet) and 8.0 ppm (doublet) due to DFDPS residues, and peaks at 7.85 ppm (broadened doublet), 7.02 (doublet of doublets) and 6.96 ppm (doublet) due to BXDO residues.

EXAMPLE 2

By a similar procedure to that given in Example 1, the same polyether synthesis was attempted with DCDPS instead of DFDPS. A powdery polymer was obtained which by GPC analysis gave an Mn=4120 and an Mw=8040, Mw/Mn=1.95. The lower molecular weight was likely a result of the reduced reactivity of the DCDPS under the chosen reaction conditions. Higher temperature and a different solvent, e.g., NMP, sulfolane, or dimethylsulfone) are likely to be necessary when the reaction with DCDPS is desired.

EXAMPLE 3

A portion (8 g) of the polyether from Example 1 was dissolved in 32 ml of NMP and a viscous solution resulted which was further diluted with 10 ml NMP. Some incompletely dissolved swollen particles were noted so the solution was heated for several hours at 120° C. which resulted in dissolution. After cooling to room temperature, this solution was pressure filtered through a 1 micron filter (over 24 hours required) and then spin coated onto 5" silicon wafers. The coated wafers were placed into an air oven at 135° C. for 30 minutes, and then placed into a nitrogen oven and heated to 200° C. for 30 minutes and 350° C. for 1 hour. The dielectric film on the wafers was coherent, homogeneous, and appeared to be defect free.

In order to measure the mechanical properties of the film, the oxide layer of one of the wafers was etched in a dilute HF bath. A free standing, coherent, creasable pale yellow film was thus obtained. This film of 9.9 micron thickness had the following mechanical properties when tested on an Instron Model 4501 per ASTM D 882-83 (Method A): Tensile Strength=83.8 MPa, Tensile Strength at Break=82.9 MPa, Tensile Elongation at Break=6%, and Young's Modulus=2.1 GPa.

What is claimed is:

1. A composition comprising a polyether of the structure:

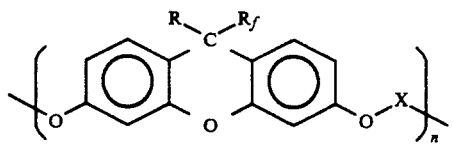

wherein $R_f$ is perfluoroalkyl of 1-16 carbon atoms,

R is selected from the group consisting of aryl, and perfluoroalkyl of 1-16 carbon atoms, n is an integer, greater than zero and —X— is a bivalent radical selected from the group consisting of aryl sulfone radical, aryl ketone radical, imide radical and mixtures thereof.

2. A composition as defined in claim 1, wherein X is an aryl sulfone radical which has the structure:

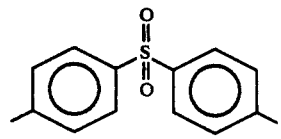

3. A composition as defined in claim 1, wherein X is an aryl ketone radical which has the structure:

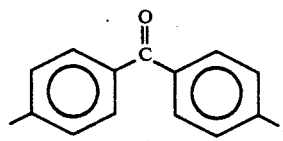

4. A composition as defined in claim 1, wherein X is an imide radical which has the structure:

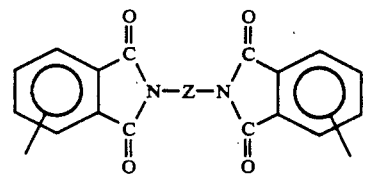

wherein Z is a bivalent aromatic radical.

5. A composition as defined in claim 1, wherein X is an imide radical which has the structure:

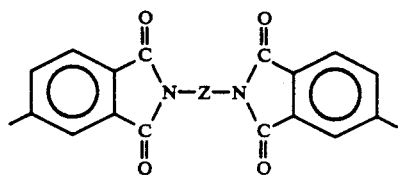

wherein Z is a bivalent aromatic radical.

* * * * *